(12) United States Patent
O'Carroll et al.

(10) Patent No.: US 10,905,555 B2
(45) Date of Patent: Feb. 2, 2021

(54) MEDICAL SECURING DEVICE FOR SECURING A CARDIAC IMPLANT DEVICE WITH A SECURING MEMBER

(71) Applicant: Medtentia International Ltd Oy, Espoo (FI)

(72) Inventors: Ger O'Carroll, Espoo (FI); Stuart Deane, Espoo (FI); Jake O'Regan, Espoo (FI); Hans-Reinhard Zerkowski, Espoo (FI); Olli Keränen, Espoo (FI)

(73) Assignee: Medtentia International Ltd Oy, Espoo (FI)

( * ) Notice: Subject to any disclaimer, the term of this patent is extended or adjusted under 35 U.S.C. 154(b) by 133 days.

(21) Appl. No.: 16/064,496

(22) PCT Filed: Aug. 16, 2016

(86) PCT No.: PCT/FI2016/050563
§ 371 (c)(1),
(2) Date: Jun. 21, 2018

(87) PCT Pub. No.: WO2017/109273
PCT Pub. Date: Jun. 29, 2017

(65) Prior Publication Data
US 2019/0000625 A1    Jan. 3, 2019

Related U.S. Application Data

(60) Provisional application No. 62/270,622, filed on Dec. 22, 2015.

(51) Int. Cl.
*A61F 2/24* (2006.01)
*A61B 17/04* (2006.01)
(Continued)

(52) U.S. Cl.
CPC ........ *A61F 2/2466* (2013.01); *A61B 17/0469* (2013.01); *A61B 17/07207* (2013.01);
(Continued)

(58) Field of Classification Search
CPC ...... A61F 2/2466; A61B 17/08; A61B 17/083
See application file for complete search history.

(56) References Cited

U.S. PATENT DOCUMENTS

2011/0054306 A1* 3/2011 del Nido ............ A61B 17/0644
600/424
2012/0330407 A1* 12/2012 Dale .................. A61B 17/0644
623/2.11
(Continued)

FOREIGN PATENT DOCUMENTS

WO    2013131925 A1    9/2013
WO    2015123597 A1    8/2015

*Primary Examiner* — Wade Miles
(74) *Attorney, Agent, or Firm* — Berggren LLP

(57) ABSTRACT

A medical securing, such as a suturing device (100) for securing a cardiac implant device (400A, 400B) with a securing member (102), like a suture. The medical securing device comprises an elongated sheath (101) extending in a longitudinal direction and having proximal (101A) and distal (101B) ends. The distal end of the elongated sheath has a support portion (101C) to support the elongated sheath to the cardiac implant device and/or to the tissue (20). The medical securing device comprises also a securing member introduction device (103) extending from the sheath (101) and having proximal (103A) and distal (103B) ends. The distal end (103B) of the securing member introduction device (103) is configured to deliver the securing member (102) to the cardiac implant device and to secure the cardiac implant device to the annulus (20) of the valve with the securing member (102).

25 Claims, 8 Drawing Sheets

(51) Int. Cl.
*A61B 17/072* (2006.01)
*A61B 17/10* (2006.01)
*A61B 17/00* (2006.01)
*A61B 17/064* (2006.01)
*A61B 34/00* (2016.01)

(52) U.S. Cl.
CPC .............. *A61B 17/10* (2013.01); *A61B 34/73* (2016.02); *A61B 2017/00243* (2013.01); *A61B 2017/00867* (2013.01); *A61B 2017/0649* (2013.01); *A61B 2217/005* (2013.01); *A61F 2230/0091* (2013.01)

(56) References Cited

U.S. PATENT DOCUMENTS

| | | | |
|---|---|---|---|
| 2014/0039511 A1* | 2/2014 | Morris | A61B 17/0467 606/110 |
| 2014/0058417 A1* | 2/2014 | Levy | A61B 17/0401 606/151 |
| 2014/0275757 A1* | 9/2014 | Goodwin | A61F 2/2466 600/37 |
| 2015/0273130 A1* | 10/2015 | McDermott | A61M 25/007 604/526 |
| 2017/0290663 A1* | 10/2017 | Erickson | A61F 2/2457 |
| 2018/0185020 A1* | 7/2018 | Deane | A61B 17/0467 |
| 2018/0368830 A1* | 12/2018 | O'Carroll | A61B 17/06166 |

\* cited by examiner

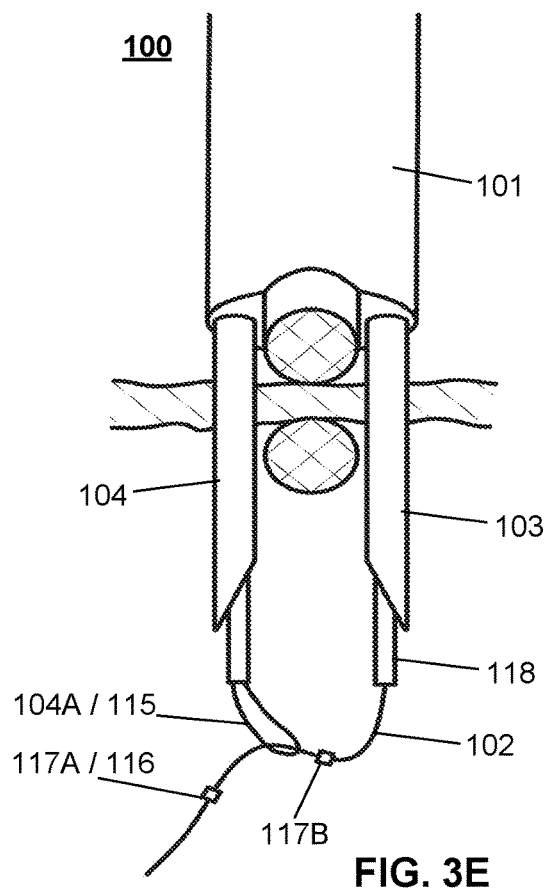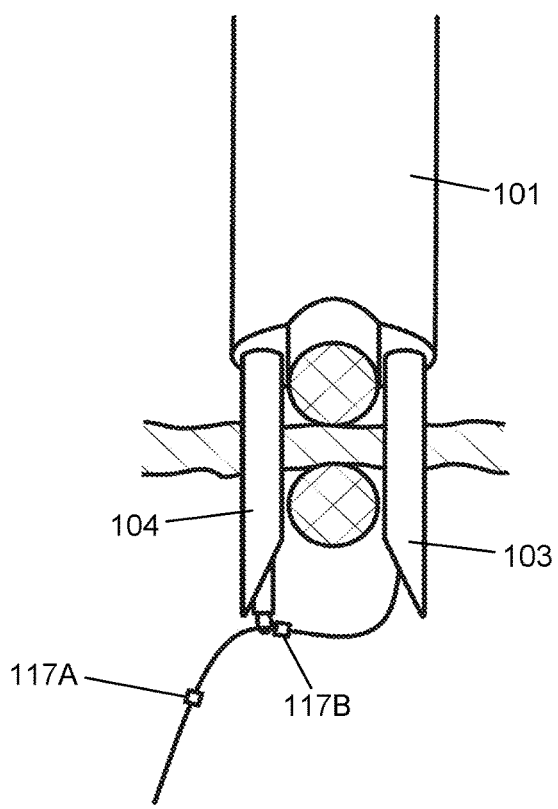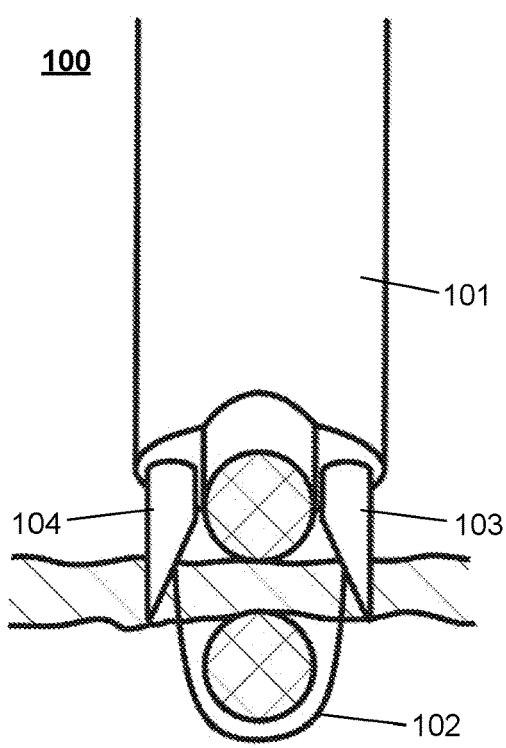

MEDICAL SECURING DEVICE FOR SECURING A CARDIAC IMPLANT DEVICE WITH A SECURING MEMBER

PRIORITY

This application is a U.S. national application of the international application number PCT/FI2016/050563 filed on 16 Aug. 2016, which claims priority of U.S. provisional patent application 62/270,622 filed on Dec. 22, 2015, the contents of all of which are incorporated herein by reference.

TECHNICAL FIELD OF THE INVENTION

The invention relates to a medical securing device for securing a cardiac implant (annuloplasty medical) device with a securing member. In particularly the invention relates to a catheter-operated or cannula-operated medical securing device for securing the cardiac implant device into an annulus of a heart valve, such as a mitral valve or tricuspid valve, comprised of valve tissue and including the annulus and a plurality of leaflets. However, the principle of the invention can also be applied for an open-heart operated medical securing device.

BACKGROUND OF THE INVENTION

FIG. 1A illustrates a portion of the heart 12, the mitral valve 18, and the left ventricle 14. The mitral valve is at its boundary circumferenced by an annulus 20. The valve has two cusps or leaflets 22, 24. Each of these cusps or leaflets 22, 24 are connected to a respective papillary muscle 27, 29 via their respective connecting chordae 26, 28. In normal healthy individuals the free edges of the opposing leaflets will close the valve by coaptation. However, for some individuals the closure is not complete, which results in a regurgitation, also called valvular insufficiency, i.e. back flow of blood to the left atrium making the heart less effective and with potentially severe consequences for the patient. FIG. 1B illustrates a mitral valve 18, in which the leaflets 22, 24 do not close properly. This commonly occurs when the annulus 20 becomes dilated. One surgical procedure to correct this is to remove a portion of the leaflet 24 and stitch the cut edges together with one another. The procedure will pull back the annulus 20 to a more normal position. However the strength of the leaflet 24 is altered. Similar problems with a less effective heart function occur if one or both leaflets are perforated to such an extent that blood is flowing towards the left atrium, although the leaflets close properly.

In some conditions of degenerated heart function, the leaflets do not present a solid surface, as in a degenerative valve disease. The leaflet may also be ruptured, most commonly at an edge of a leaflet, resulting in an incomplete coaptation. Hence, cardiac devices and methods are developed for repairing of one or more leaflets of a heart valve, or other related anatomical structures, such as the chordae attached to the ventricular side of leaflets.

FIGS. 2A and 2B illustrate a prior art cardiac implant device and method for repairing of one or more leaflets of a heart valve as is described in the applicant's previous EP-patent (EP 1 853 199 B1), where the device 40 comprises a first and a second loop-shaped support 42, 44, which are connected to each other by means of a connecting part 48 so as to form a coil-shape. The coil-shape of the device is advantageous during insertion, since the device 40 may then be rotated into position, as described in the patent in more details. One of the supports 44 may be open, e.g. C or D or any other anatomical shaped such that the support 44 presents an end to lead the movement of the support 44 when being rotated into position. The position of the supports 42, 44 are secured by fasteners 56, which are inserted and fastened by hand or small screwdriver.

It is found that the prior art cardiac implant devices, such as depicted above, work very well, but there are still some disadvantages relating to the securing of the cardiac device into the annulus of the heart valve. The cardiac devices are typically manually sutured by a traditional needle and yarns, which is time consuming, because in practise it is needed at least seven knots to be tied in order to have even some certainty that the device is secured. In addition, if the device is sutured by one yarn, which has a drawback namely if one or more knots is/are loosen or the yarn is broken, then the whole securing will come loosen or broken.

In addition with the previous suturing devices it has been difficult to suture in the correct position, thereby providing insufficient suturing strength, and also resulting in a very time consuming procedure, which increases the risks for the patient. Previous suturing devices are also not sufficiently compact for catheter based procedures, for example. There is therefore a need to provide an improved suturing device that solves these issues.

The cardiac implant devices are also secured by screws. However, the screws are very small, the assembling, positioning and controlling of which are extremely difficult. The screws must be inserted through the both the first and second (upper and lower) loop-shaped support portions 42, 44 (tiny holes in both of the portions), which is highly demanding, because if the first screw is tightened too much, it will distort the portions little bit and thus misaligning the other holes and thereby making it impossible to inserting the other screws. Furthermore there is a huge risk to drop the small screws into the cardiac structure, because for example any safety blankets cannot be used. In addition also magnetic material cannot be used due to possible later magnetic imaging.

SUMMARY OF THE INVENTION

It is an object of the invention to alleviate and eliminate the problems relating to the known prior art. Especially the object of the invention is to provide a medical securing device for securing a cardiac implant device with a securing member into an annulus of a heart valve in an easy, fast, safe and accurate manner with a high degree of control.

The object of the invention can be achieved by the features of independent claim.

The invention relates to a medical securing device for securing a cardiac implant device with a securing member into an annulus of a heart valve according to claim 1. The medical securing device may be for example a suturing device for suturing the cardiac implant device into the annulus of the heart valve. The cardiac implant device may be any cardiac implant device known from prior art, such as described in FIGS. 1-2 and having ring or double ring (helical) shape especially for mitral implant, but also any further application or other device, like a ventrical or atrium or septum correction patch or device or for example a heart valve prosthesis.

According to an embodiment of the invention a medical securing device for securing a cardiac implant device comprises an elongated sheath extending in a longitudinal direction and having proximal and distal ends. The distal end of the elongated sheath comprises a support portion to support the elongated sheath to the cardiac implant device and/or to the tissue. The medical securing device comprises also a securing member introduction device, like a catheter, extending from the sheath and having proximal and distal ends, and having a needle or tip portion configured to penetrate or puncture into or through the tissue. The distal end of the securing member introduction device is configured to introduce, such as deliver and possibly manipulate, like bend or twist, the securing member, such as a suture, to the cardiac implant device and thereby to secure at least portion of the cardiac implant device to the annulus of the valve with the securing member.

According to an embodiment the medical securing device may additionally comprise a retrieval device with a retrieval unit at a distal end thereof. The retrieval device may also be implemented as a catheter having a needle or tip portion configured to penetrate or puncture into or through the tissue. When the retrieval device is extended through the tissue, the retrieval unit is configured to capture a portion of the securing member, such as a portion of the suture or end portion of a staple or other securing member portion disclosed elsewhere in this document. After capturing the portion of the securing member, the medical securing device is used for securing the cardiac implant device by the securing member (or at least by portion of it) to the annulus of the valve.

The securing member introduction device as well as also the retrieval device can have different types of tip portions. Using of atraumatic type tip portion is very advantageous namely it does not cut the tissue as such but rather it penetrates between the tissue fibers and displaces them making no cut into the tissue.

Depending on the application the securing member may be a suture, staple, helical clip, locking clip, spring clip, or circular clip, and comprising shape memory material, metal or polymer or other suitable material. In embodiments describing the current invention the suture is used as an advantageous example of the securing member. However it should be understood that also other type securing members can be used.

The present invention offers advantages over the known prior art, such as an easy, safe, precise and time saving manner to reliable securing the cardiac implant device to the annulus of the valve with the securing member. In addition, the present invention provides for a compact medical securing device, such as a suturing device, that facilitates suturing and fixation of a cardiac implant device, such as an annuloplasty implant, to the tissue. For example it is particularly easy to suture beneath a tissue wall, such as the annulus of a heart valve, from the opposite side facing an operator, which otherwise is cumbersome due to the limited visibility. The compact medical securing device allows it to be catheter deliverable for a minimally invasive procedure. Furthermore, when using the catheter-operated or cannula-operated medical securing device, risks for having any medical drawbacks or symptoms are much lower than e.g. in the traditional open-heart operation. Also the patient recovery process is much faster. In addition the using of the medical securing device according to the present invention is very clear, logical and straight for the user, namely the securing operation can be done advantageously by one continuous movement.

The exemplary embodiments presented in this text are not to be interpreted to pose limitations to the applicability of the appended claims. The verb "to comprise" is used in this text as an open limitation that does not exclude the existence of also un-recited features. The features recited in depending claims are mutually freely combinable unless otherwise explicitly stated.

The novel features which are considered as characteristic of the invention are set forth in particular in the appended claims. The invention itself, however, both as to its construction and its method of operation, together with additional objects and advantages thereof, will be best understood from the following description of specific example embodiments when read in connection with the accompanying drawings.

BRIEF DESCRIPTION OF THE DRAWINGS

Next the invention will be described in greater detail with reference to exemplary embodiments in accordance with the accompanying drawings, in which.

DETAILED DESCRIPTION

FIGS. 1A-1B and 2A-2B are already discussed in more details in connection with the background of the invention portion above.

Figure 9B:
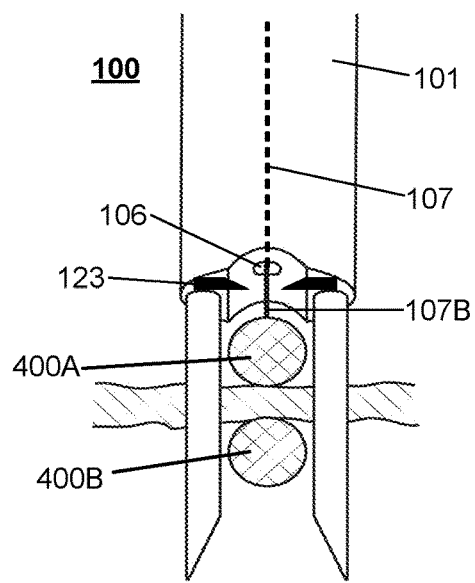
Figure 9A:
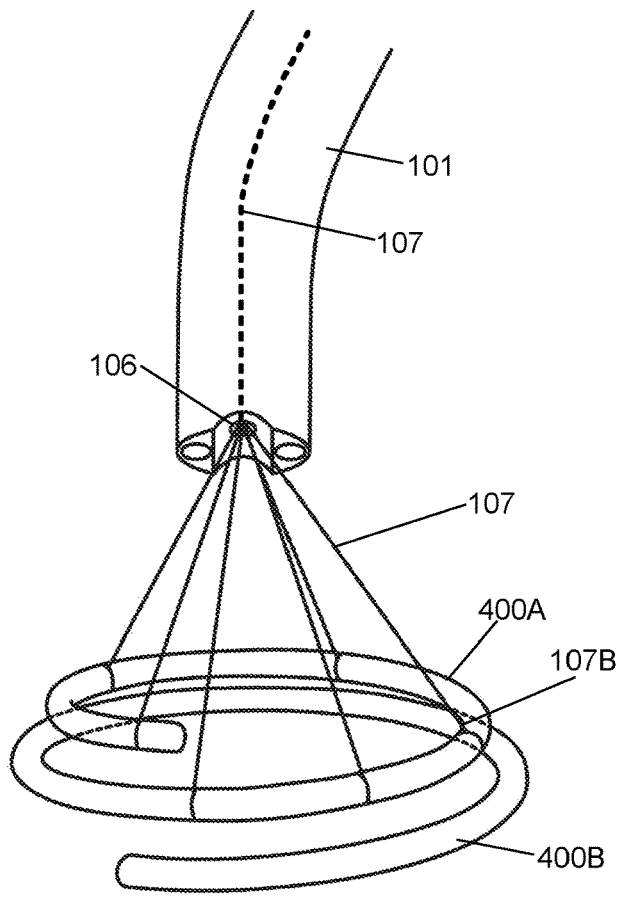
Figure 10A:
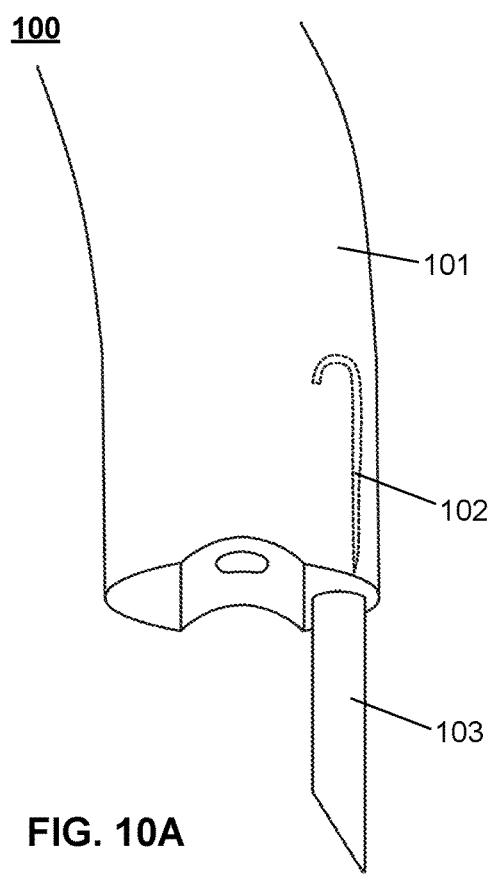
Figure 10B:
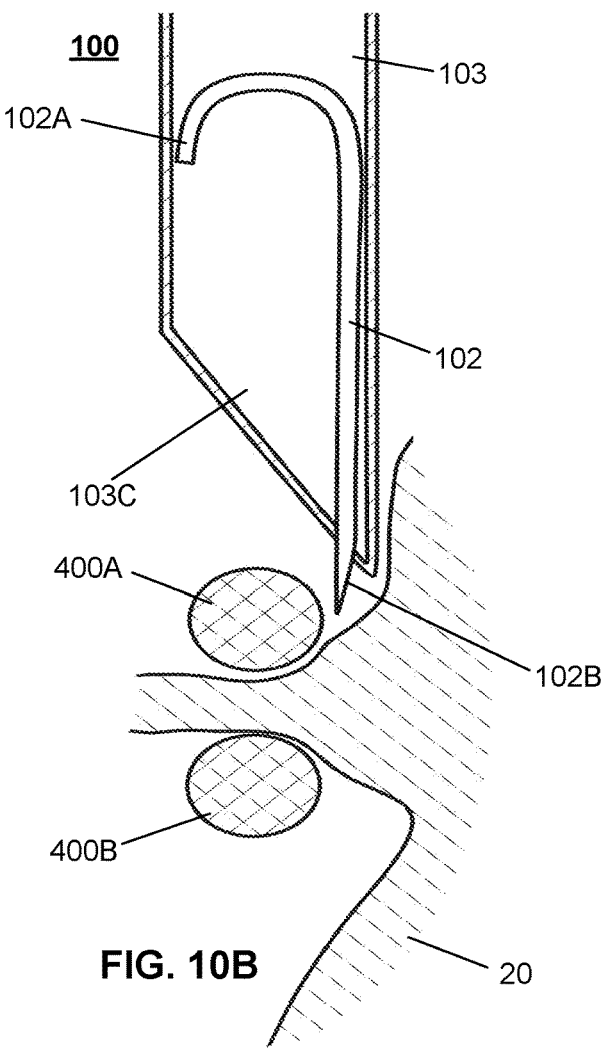
Figure 10C:
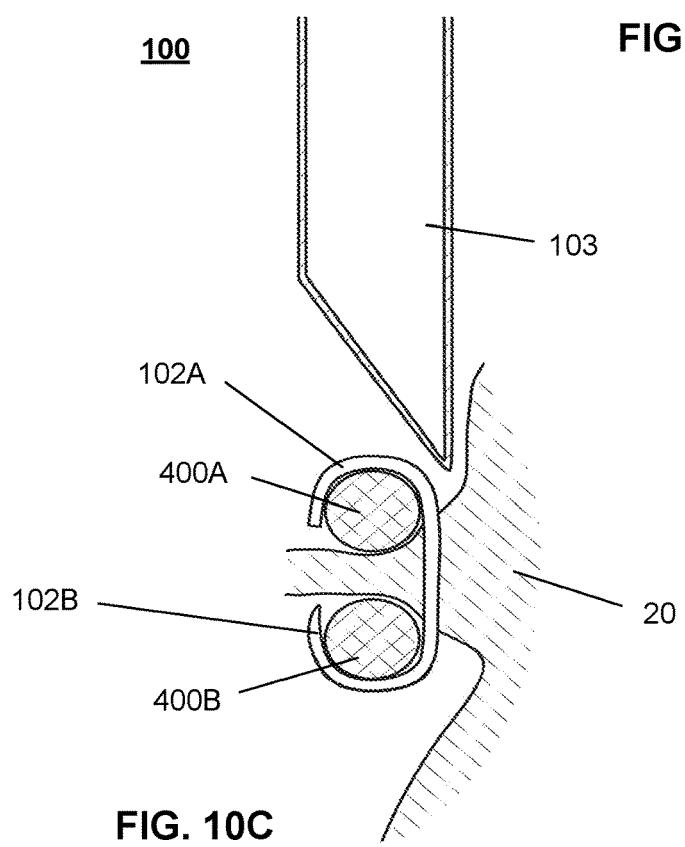

FIGS. 3A-12 illustrate examples of medical securing devices 100 for securing a cardiac implant device 40, 400A-400B according to advantageous embodiments of the invention, and in particularly a suturing device 100, even if the medical securing device can also be applied with another types of the securing members as discussed elsewhere in this document (see e.g. FIG. 10A-10C, as an example). The medical securing device 100 comprises an elongated sheath 101 extending in a longitudinal direction and having proximal 101A and distal 101B ends. The distal end of the elongated sheath comprises a support portion 101C to support the elongated sheath to the cardiac implant device directly or to the tissue 20 opposite e.g. the lower portion ring 400B of the cardiac implant device (as can be seen e.g. in FIG. 4E, 4F).

The medical securing device 100 comprises a securing member introduction device 103 like a catheter, extending from the sheath 101 and having proximal 103A and distal 103B ends. The distal 103B end comprises a needle or tip portion 108 configured to penetrate or puncture into or through the tissue 20. The distal end 103B of the securing member introduction device is configured to introduce the securing member 102 to the contact with the cardiac implant device 400A, 400B, and thereby to secure the upper and/or lower portion 400A, 400B of the cardiac implant device to the annulus 20 of the valve with the securing member 102.

The medical securing device 100 may comprise advantageously also a retrieval device 104 with a retrieval unit 104A at a distal end 104B thereof. The retrieval device 104 may also be implemented as a catheter having a needle or tip portion 109 configured to penetrate or puncture into or through the tissue 20. When the retrieval device 104 is extended through the tissue, the retrieval unit 104A is configured to capture a portion of the suture 102. After capturing the portion of the suture 102, the cardiac implant device 400A, 400B can be secured by the portion of the securing member 102 to the annulus 20 of the valve.

Depending on the application and used securing member 102 the retrieval unit 104A can be used also for capturing an end portion of the staple, clip or shape memory material and possibly also twist or bend it around or in connection with the cardiac implant device 400A, 400B or to the annulus 20 of the valve.

It is to be noted that depending on the application and used securing member 102 the medical securing device 100 of the invention can also be operated by the securing member introduction device 103 and without the retrieval members 104, 104A, as is described in FIGS. 10A-C and 11C, for example, where the securing member introduction device 103 can be used for example introducing, such as just delivering a staple like securing member 102. Depending on the application and used securing member 102 the distal end 103B of the securing member introduction device 103 may have minor structural differences, but the same inventive principle applies for all. For example the securing member introduction device 103 may deliver the suture 102 from the distal opening 103C of said suture delivery catheter 103 at a distal end 103B thereof, whereupon the retrieval device 104 with a retrieval unit 104A is advantageously required for capturing the portion of the suture. In other application the securing member introduction device 103 may introduce the staple, and press and bend it at least partially around cardiac implant device. The securing member introduction device 103 and/or retrieval device 104 with a retrieval unit 104A can also be used for twisting or otherwise providing, positioning and securing the securing member in an appropriate way.

Figure 1A:
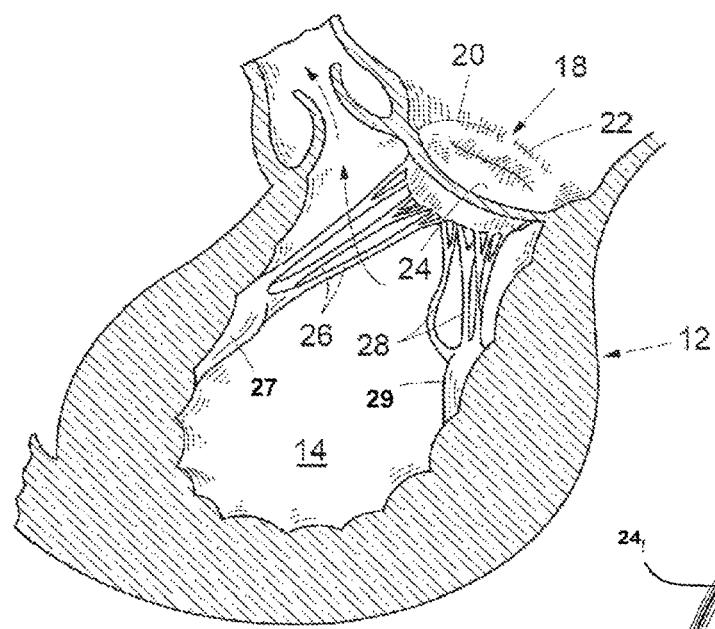
FIGS. 1A-1B illustrate schematically a portion of a heart and mitral valve.
Figure 1B:
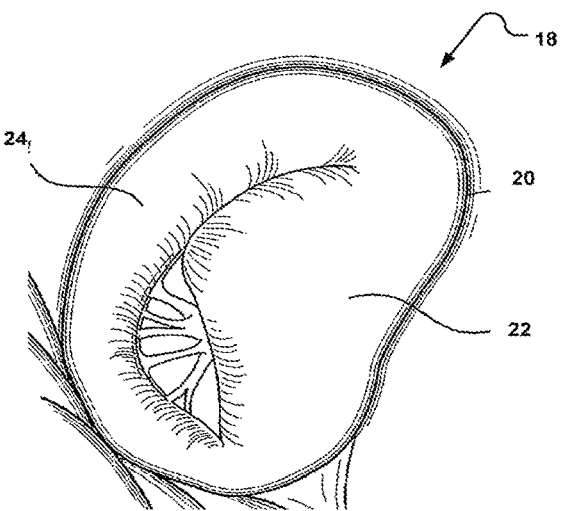
Figure 2A:
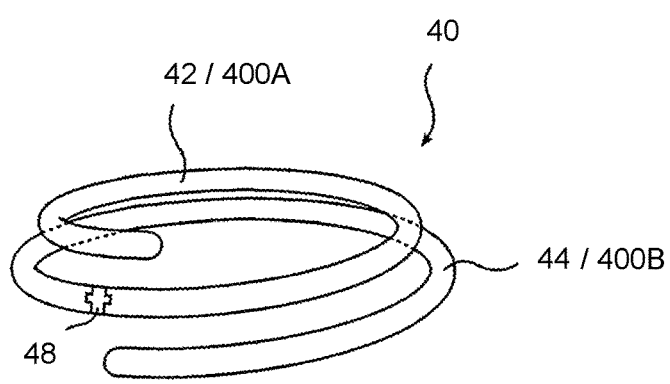
FIGS. 2A-2B illustrate a prior art cardiac implant device for repairing of one or more leaflets of a heart valve.
Figure 2B:
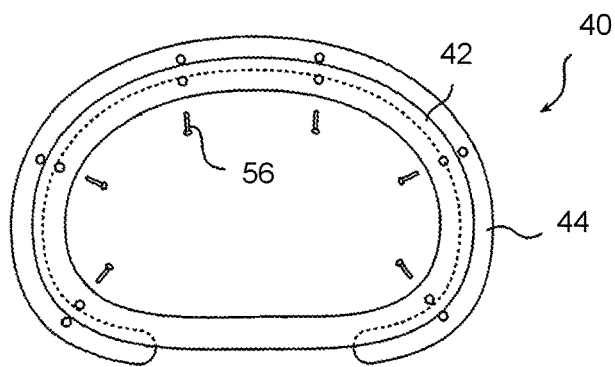
Figure 3A:
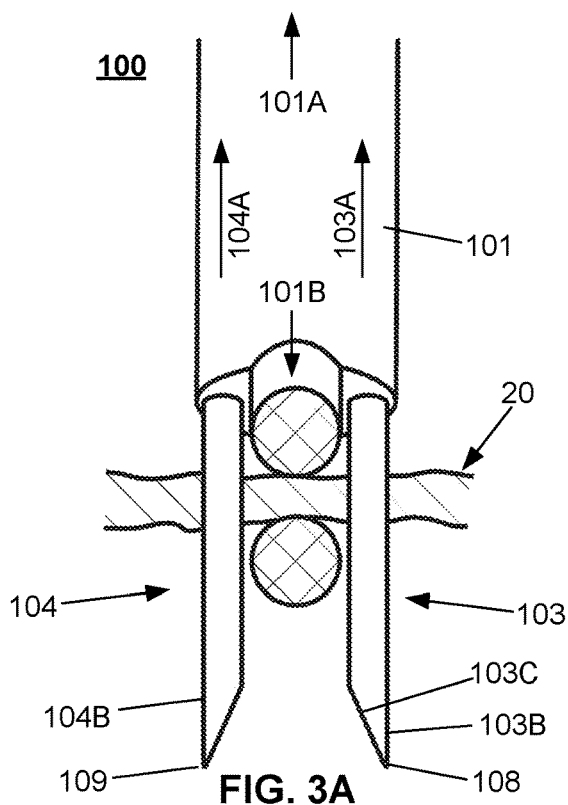
FIGS. 3A-12 illustrate examples of medical securing devices according to advantageous embodiments of the invention.

The medical securing device 100 is typically configured so that the retrieval unit 104A and the securing member 102 extend at least a distance from the sheath 101 corresponding to the length of said cardiac implant device 400A, 400B between said proximal and distal portions thereof, so beyond a lower part 400B of the cardiac implant device in a longitudinal direction, as can be seen in FIG. 3A.

Figure 3B:
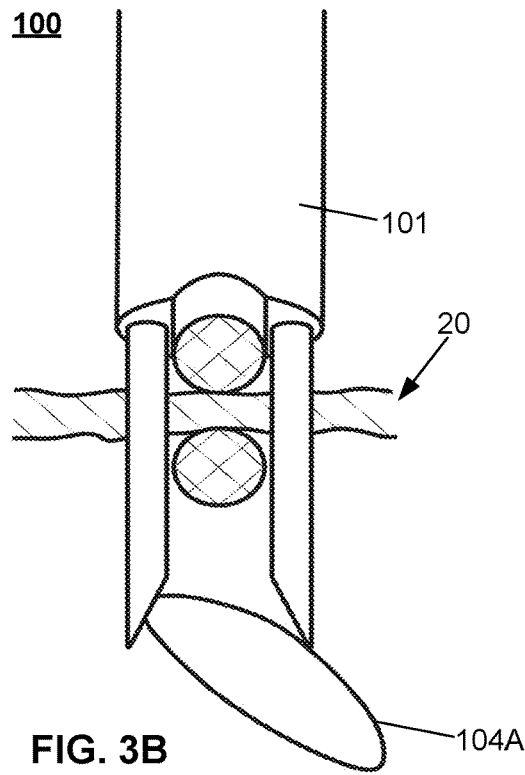
Figure 3C:
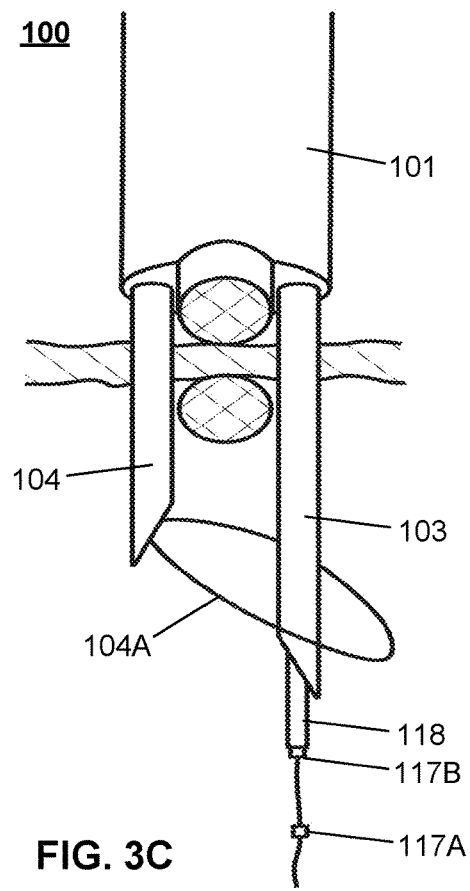
Figure 3D:
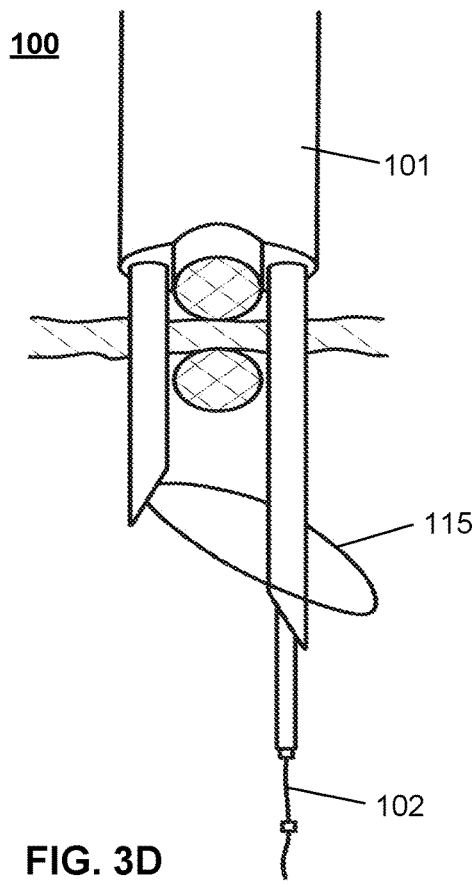
Figure 4A:
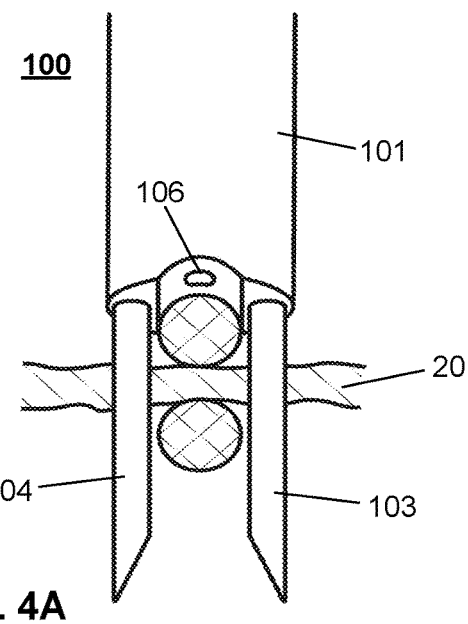
Figure 4B:
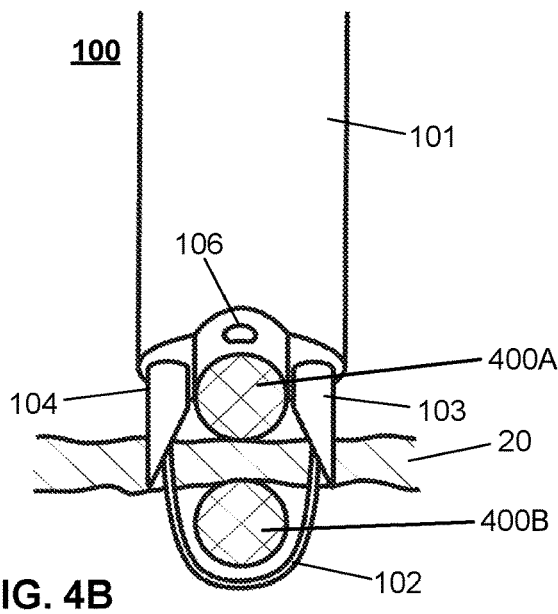
Figure 4C:
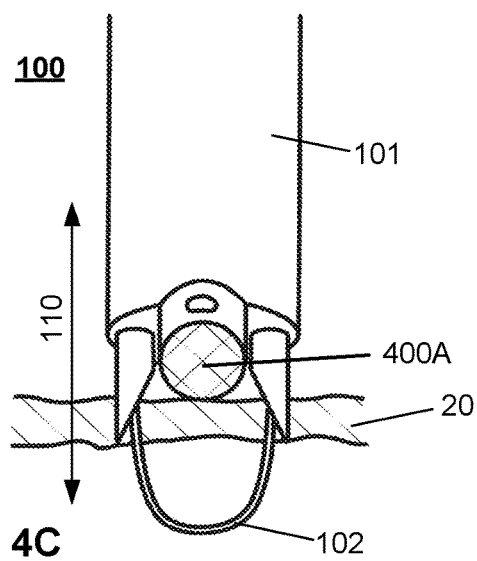
Figure 4D:
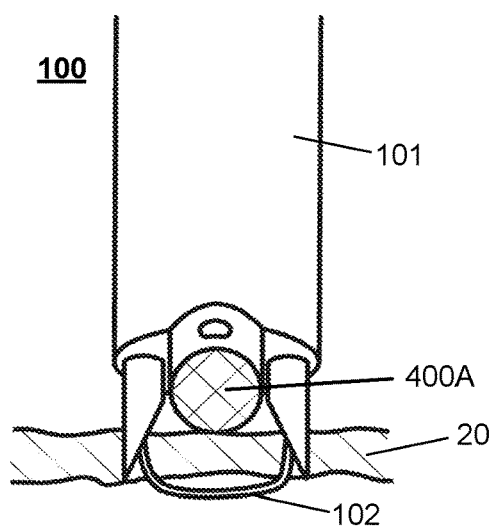
Figure 4E:
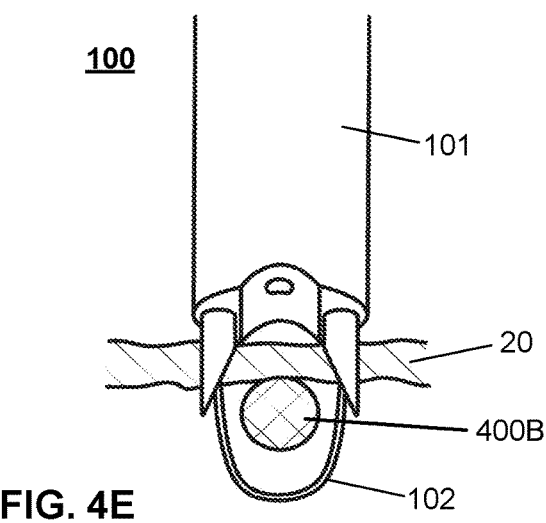
Figure 4F:
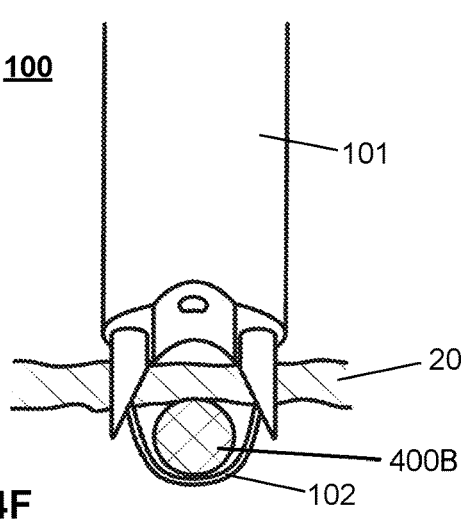

The retrieval device 104 and/or the retrieval unit 104A may be operated so that the retrieval unit 104A can be controlled or moved towards the securing member introduction device 103 across the distal part, after having penetrated the tissue 20, as can be seen e.g. in FIG. 3B. For example the form or shape of the retrieval device 104 may be so that it forces the retrieval unit 104A towards the securing member introduction device 103, or it may be operated, such as turned by using an operation arm 120. The retrieval unit 104A may also comprise shape memory material being resiliently biased to move towards the securing member introduction device 103 when being pushed out from said retrieval device 104. It is to be noted that in Figures it is the retrieval device or unit 104, 104A which is moved towards the securing member introduction device 103, but also the securing member introduction device 103 can be moved towards retrieval device or unit 104, 104A in a similar manner. The retrieval device 104 and/or retrieval unit 104 may be also independently movable from the securing member introduction device 103 and according to an embodiment they can be turned around the longitudinal axis of the devices 103, 104 for example via controlling by the operation arm 120.

Advantageously the retrieval unit 104A may comprise a loop 115, which can be positioned beneath the securing member introduction device 103 and operated so that the securing member introduction device 103 may then introduce the distal end of the suture 102 to the loop. The suture may comprise a proximal increased diameter portion 117B to be engaged by a pusher 118, which is movable inside the securing member introduction device 103 so that said securing member 102 can be pushed distally from the securing member introduction device 103, as can be seen e.g. in FIG. 3C, 3D.

The retrieval unit 104A can then be used for capturing the portion of the suture 102, whereby the portion of the suture can be pulled towards the retrieval device 104. The suture 102 comprises advantageously also a distal increased diameter portion 117A so to help capturing the suture by the retrieval unit 104A and that the suture would not be lost when captured and pulled by the retrieval unit 104A, as can be seen e.g. in FIG. 3F. According to an embodiment the retrieval unit 104A may comprise a magnet and the suture (or other securing member) 102 a metal portion 116 so to be attracted by said magnet and thereby capturing the suture. When the suture is captured and pulled towards, over or across the of said cardiac implant device 400B locating advantageously between the securing member introduction device 103 and the retrieval device 104, the cardiac implant device can then be secured into the tissue 20 by the securing member, as can be seen in FIGS. 3E-3G, and the retrieval device 104 with the retrieval unit 104A and the securing member introduction device 103 can be pulled back into the sheath 101.

The sheath 101 may also comprises a conduit 106 between the proximal and distal ends 101A, 101B thereof for introducing under pressure via said conduit into the distal end 101B or to the support portion 101C of the sheath 101, as can be seen e.g. in FIGS. 4A-4F. The applied under pressure can be used to suck the device 100, 101 for a firm connection with the surface of the cardiac implant device 400A or tissue 20 and thereby to support the sheath 101 or the support portion 101C to the cardiac implant device 400A either directly or via the tissue 20, when only the lower portion of the cardiac implant device 400B is used. The sheath 101 or the support portion 101C can also be supported to the tissue 20 via the force induced by the under pressure. The under pressure with the support portion 101C applies advantageously counterforce for the introduction movement 110 of the securing member 102. As can be seen in Figures, the support portion 101C advantageously comprises a form or shape, such as a concave portion in order to be more mechanically compatible with the shape of the cardiac implant device 400A and thereby better support the medical securing device 100 to the cardiac implant device 400A during the operation.

Figure 8:
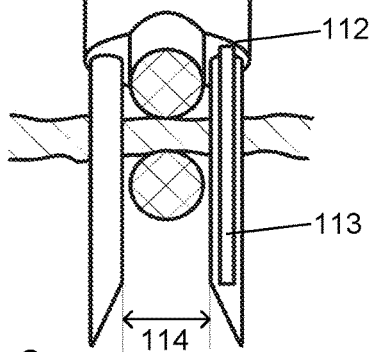

The retrieval device 104 and the securing member introduction device 103 are advantageously separated by a radial distance 114 corresponding at least to a width of the cardiac implant device 400A, 400B (see FIG. 8). In addition the retrieval device 104 and the securing member introduction device 103 are being positionable on either side of said cardiac implant device 400A, 400B in said radial direction.

Figure 5A:
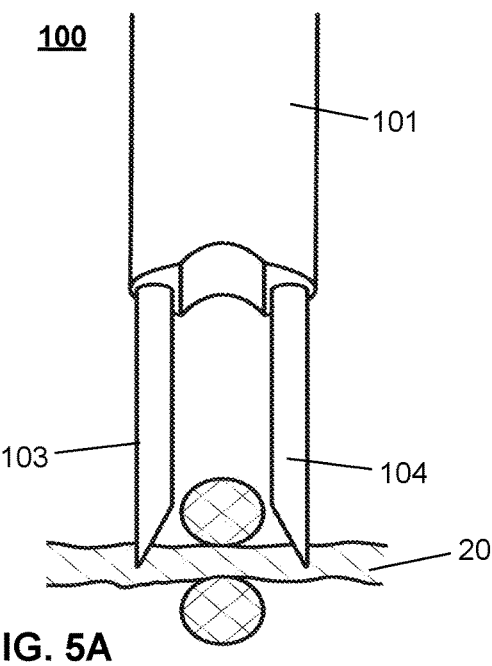
Figure 5B:
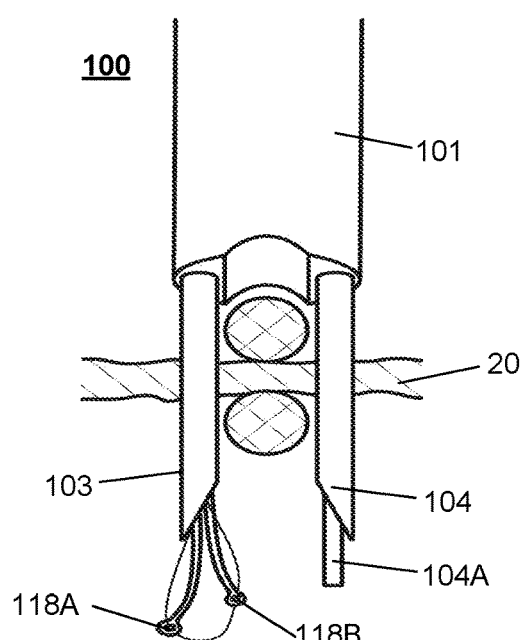
Figure 5C:
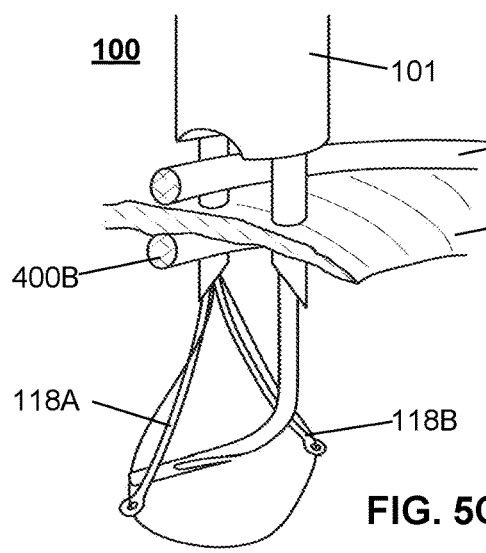
Figure 5D:
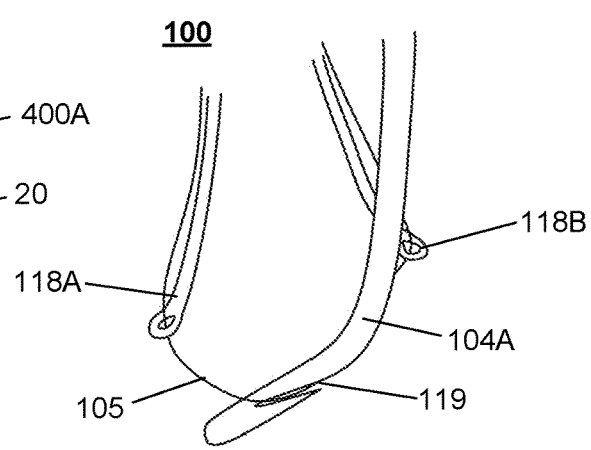
Figure 5E:
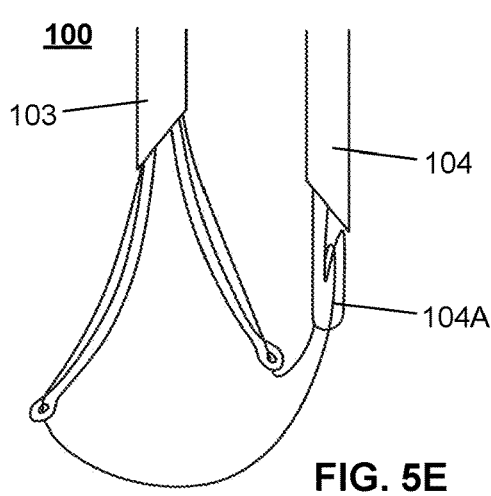
Figure 5F:
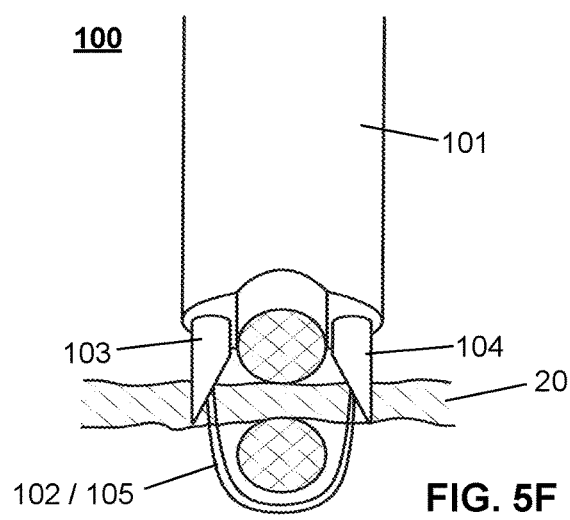
Figure 6:
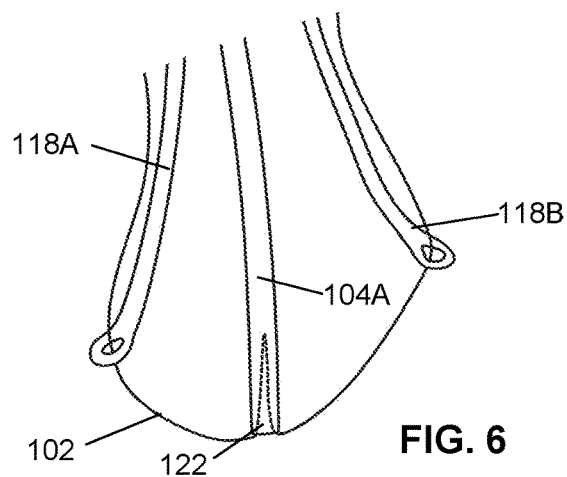

The securing member introduction device 103 as well as the retrieval device 104 and the retrieval unit may have different forms, as can also be seen in FIGS. 5A-5F, where the securing member introduction device 103 according to an embodiment comprises radially displaceable arms 118A, 118B holding the suture 102. The radially displaceable arms 118A, 118B can be pushed out from the securing member introduction device 103 (catheter), whereupon the arms may be resiliently biased to diverge and thereby form an extended shape when displaced outside the securing member introduction device 103, as can be seen in FIG. 5B, 5C. The radially displaceable arms 118A, 118B advantageously introduce the suture so to form a looped form, or a protrusion portion 105 or bridge 105 with a portion of the suture 102.

The retrieval unit 104A may in turn comprise a hook-shaped portion 119 for engaging and capturing the portion 105 of said looped shape suture 102. Alternatively, or in addition to, the retrieval unit 104A may comprise a suction tip 122 for engaging and capturing the portion 105 of the suture 102 via the under pressure applied to the suction tip 122, whereupon the form of the suture 102 does not need to be even a loop structure. After capturing the portion 105 the retrieval unit 104A can be pulled with the portion 105 of the suture 102 and thereby securing the cardiac implant device 400A, 400B to the tissue 20. It is to be noted that the under pressure of the suction tip 122 can be applied during the whole capturing, pulling and securing operation in order to ensure that the captured suture is not lost.

The cardiac implant device 400A, 400B can be delivered into its position by an own catheter, for example. According to an advantageous embodiment of the invention the cardiac implant device 400A, 400B may be provided with at least one guiding wire 107, as can be seen in FIGS. 9A, 9B for guiding the medical securing device 100 into a correct position. The distal end 107B of the guiding wire 107 is advantageously fixed to the cardiac implant device 400A and the proximal end (not shown) is left outside the body of the patient to be operated. Thus the guiding wires 107 left outside the body (after removing the cardiac implant device delivering catheter) can be used as guiding the elongated sheath 101 to its correct position in relation to the positioned cardiac implant device 400A, 400B and thereby enabling suitable and appropriate suturing procedure. Thus, according to an embodiment the elongated sheath 101 comprises a conduit 106 between the proximal and distal ends 101A, 101B thereof, which is used for receiving the at least one guiding wire 107, when the medical securing device 100 is introduced, advantageously via the catheter-operation, to its position. More precisely the guiding wire(s) 107 is/are introduced through the conduit 106 from the distal end to the proximal end of it.

It is to be noted that there might be a number of the guiding wires 107 used, which can be received either one by one through the conduit 106 or all at the same time. If they are received one by one, the elongated sheath 101 or medical securing device 100 must be pulled out each time after suturing the portion of the cardiac implant device 400A, 400B and again a next guiding wire 107 must in used to guide the medical securing device 100 into the next position and to secure the cardiac implant device 400A, 400B at said next position. When receiving all the guiding wires 107 at the same time the securing operation is much faster, because there are no needs to pull out the securing or suturing device 100 between securing the different portions of the cardiac implant device 400A, 400B and guided by each of said guiding wires 107. When all guiding wires 107 are received at the same time, each of said portions of the cardiac implant device 400A, 400B to be secured can be find by tightening one of the guiding wire 107 in turn and thereby guiding the medical securing device 100 (elongated sheath 101) along said tightened guiding wire 107 to the correct position in relation to the cardiac implant device 400A, 400B. The guiding wires 107 may have colour codes, number codes or any other identification codes so that different wires can be identified or separated from each other.

It is to be noted that the under pressure can also be used for capturing and receiving the guiding wires 107 (so when located outside the body after delivering the cardiac implant device) through said conduit 106. The use of the guiding wires offers also other advantages, namely the guiding wire 107, especially when tightened, can be used to guide and support the support portion 101C to the cardiac implant device 400A, 400B. Additionally the elongated sheath 101 together with the guiding wire 107 provides a system so that a counterforce can be applied for the introduction movement 110 of the securing member 102 to the cardiac implant device 400A, 400B, especially when tightened, thereby also enabling securing, supporting or stabilizing the support portion 101C of the distal end 101B of the elongated sheath 101 to the cardiac implant device 102 both in the longitudinal but also in the lateral directions.

In addition the distal end 101B of the elongated sheath 101 may comprise a cutting member 123 for cutting the guiding wire 107 advantageously in the vicinity of the cardiac implant device 400A, 400B after guiding and securing (suturing), as is described in FIG. 9B. The cutting member 123 is advantageously operable via the operation arm 120 from the proximal end of the device. After cutting short length of the guiding wire (e.g. 5-7 mm) might be left.

The distal end 101B of the elongated sheath 101 may also comprises a guiding trail 112, such as a groove, slot, as is described in FIG. 8. Respectively the tip portion of the securing member introduction device 103 and/or the retrieval device 104 may also comprise a projection 113 as a counterpart for the guiding trail (or vice versa). The guiding trail 112 and projection 113 thereby guide the tip portion of the securing member introduction device 103 and/or the retrieval device 104 so to pierce the tissue 20 without substantive twisting around the longitudinal axis of the tip portion of the device 103, 104. By this it can be ensured that the position or angle or hook-shape or needle eye is in a right or suitable position in relation to the cardiac implant device 400A, 400B, for example.

Figure 7:
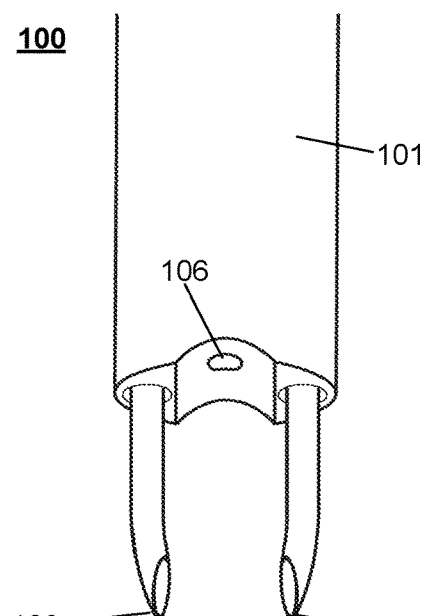

FIG. 7 illustrates an example of a tip portion 108, 109 of the securing member introduction device 103 and retrieval device 104. The used tip portion is advantageously an atraumatic type tip portion 108, 109, which is very advantageous namely it does not cut the tissue as such but rather it penetrates between the tissue thread and displaces them making no cut into the tissue.

FIGS. 10A-10C illustrate a staple 102 as an example of another type securing member according to an advantageous embodiment of the invention. As can be seen in FIGS. 10A-10C one end 102A, 102B of the staple may be bendable at least partially around or into the cardiac implant device 400A, 400B. The proximal end 102A of the staple may have a hook-like form, which is pressed or positioned by the distal end 103B of the securing member introduction device 103 (or by a piston movable inside distal end the of the securing member introduction device 103) around the cardiac implant device 400A, 400B or into the annulus tissue 200 for example if there is only one ring, such as a lower ring 400B used of the cardiac implant device. The distal end 102B of the staple is advantageously straight, whereupon it must be somehow forced to be coupled around the lower ring 400B of the cardiac implant device or into the annulus tissue 20. According to the invention this can be done by the retrieval device 104 and the retrieval unit 104A (as is described in the connection of FIGS. 3A-3G, for example), which is used to capture the distal end 102B of the staple and bend it around the lower ring 400B or into the tissue 20. According to an example the staple or at least portion of the distal end of it may comprise shape memory material being resiliently biased to move towards the retrieval device or unit 104, 104A (not shown in FIGS. 10A-10C), or cardiac implant device 400A, 400B or tissue 20 when being pushed out from the securing member introduction device 103. It should be noted that according to an embodiment the staple like securing member 102 can be introduced and secured just by using the securing member introduction device 103, whereupon there is necessarily no need for the retrieval (or other contributory) device or the retrieval unit.

FIGS. 11A-11E illustrate examples of embodiment describing the medical securing device 100 and the elongated sheath 101 and especially the distal end 101B of the elongated sheath 101. As can be seen in FIGS. 10A and 10B, the securing member introduction device 103 as well as the retrieval device 104 can be retracted inside or into the sheath 101 so that especially the possibly sharp tip portions do not cause any damage during introduction of the elongated sheath 101. Again the securing member introduction device 103 as well as the retrieval device 104 are also extendable from the sheath 101. According to an embodiment the medical securing device 100 may be implemented just by the securing member introduction device 103 and without the retrieval device 104, as is the case in FIG. 10C. The retraction and ejection of the devices 103, 104 can be controlled by using the operation arm 120.

Figure 11A:
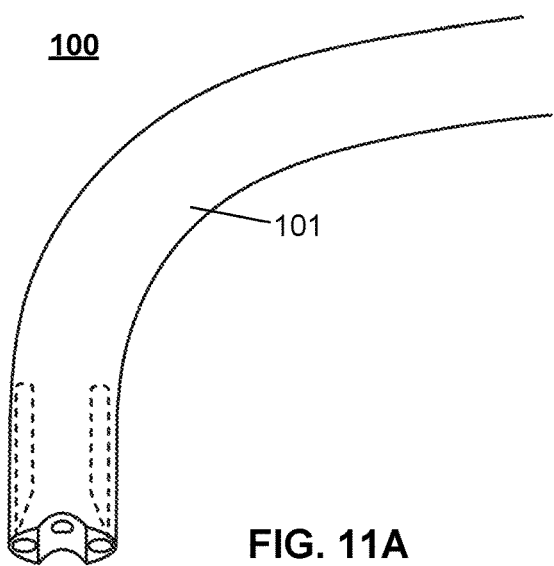
Figure 11B:
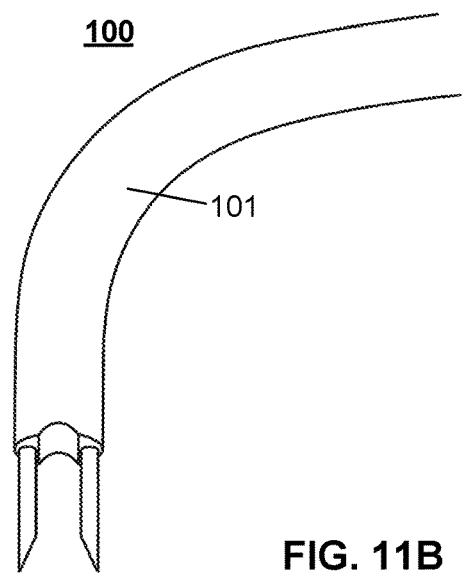
Figure 11C:
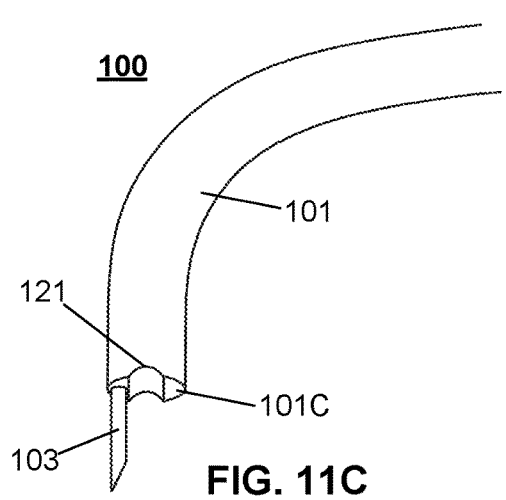
Figure 11D:
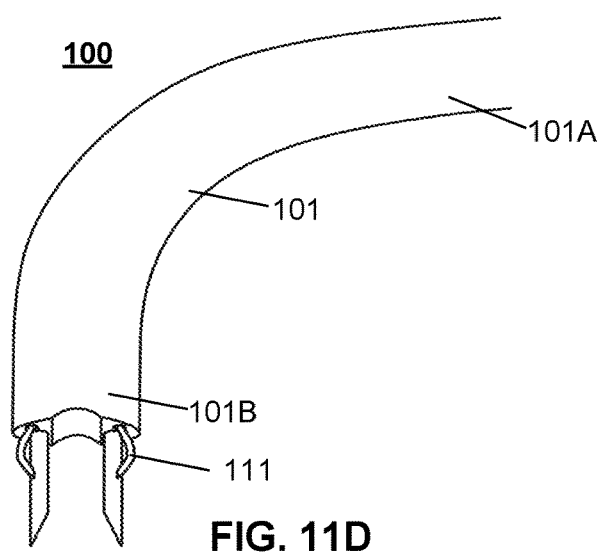
Figure 11E:
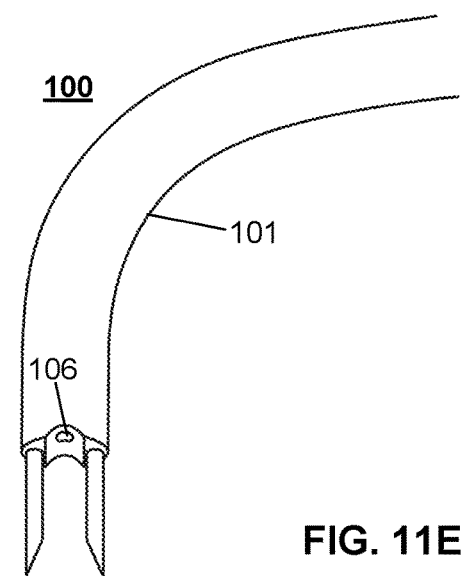
Figure 12:
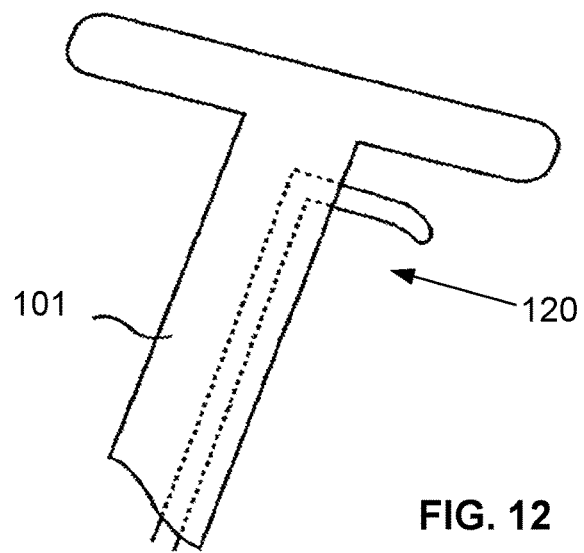

The medical securing device 100 or more precisely the distal end 101B of the elongated sheath 101 may also comprise a locking member 111, which is advantageously configured to lock the distal end 101B of the elongated sheath 101 to the cardiac implant device 400A, 400B or to the tissue 20. The locking member 111 can be implemented e.g. by a finger or spring, and it might be made of or comprise shape memory material. It may be operable also from the proximal end of the elongated sheath so via operation arm 120, for example. In addition, FIG. 11E illustrates an example of the distal end 101B of the elongated sheath 101 showing also the conduit 106.

In addition, as can be seen in the Figures, the distal end 101B or the supporting portion 101C of the elongated sheath 101 comprises a recess 121, which is advantageously shaped so to receive and thereby to support the distal end 101B/supporting portion 101C of the elongated sheath 101 to the upper or lower portion 400A, 400B of the cardiac implant device during the introduction of the securing member 102.

Moreover, the distal end 103B of the securing member introduction device 103 may also comprises a design (e.g. bended tip of the tip portion of the needle 108, 109), which thereby introduces the securing member 102 in an angle in relation the upper portion of the cardiac implant device 400A so that the securing member extends through the annulus of the valve and bends at least partially around or partially into the lower portion of the cardiac implant device. The distal end 103B of the securing member introduction device 103 may also be configured so that it can be controlled, such as turned or bent e.g. by the operation arm 120, to introduce the securing member 102 in the angle in relation the upper portion of the cardiac implant device memory material.

The operation arm 120 is locating advantageously in the proximal end 101A of the elongated sheath 101 so that it can be easily operated by the user. The operation arm 120 can be used, among the things described elsewhere in this document, especially for moving the distal end 103B of the securing member introduction device 103 and thereby introducing the securing member 102 to the cardiac implant device. In addition operation arm 120 can be used for introducing the securing member 102 and/or for moving the distal end of the retrieval device 104 and thereby capturing the portion of the securing member 102. Furthermore the operation arm 120 can also be used for securing the portion of the securing member 102 to the cardiac implant device 400A, 400B and/or to the annulus 20.

The invention has been explained above with reference to the aforementioned embodiments, and several advantages of the invention have been demonstrated. It is clear that the invention is not only restricted to these embodiments, but comprises all possible embodiments within the spirit and scope of the inventive thought and the following patent claims. For example when the suture is demonstrated, it is only as an example and also other types of securing members can be used. In addition it is to be understood that the suture may be a stitch, yarn, or fiber comprising e.g. steel, silk or other suitable material. The features recited in dependent claims are mutually freely combinable unless otherwise explicitly stated.

The invention claimed is:

1. A medical securing device for securing a cardiac implant device with a securing member, being a fastener, wherein the medical securing device comprises:
    an elongated sheath extending in a longitudinal direction having proximal and distal ends, and at least guiding wire,
    the distal end of the elongated sheath having a support portion to support the elongated sheath to the cardiac implant device and/or to the tissue, the support portion comprising a concave portion that is configured to be compatible with the shape of the cardiac implant device, and
    a securing member introduction device extending from the sheath and having proximal and distal ends, where the distal end of the securing member introduction device is configured to introduce the securing member to the cardiac implant device to secure the cardiac implant device to the annulus of the valve with the securing member, and
    where the elongated sheath comprises a conduit between the proximal and distal ends thereof for receiving the at least one guiding wire, the distal end of the at least one guiding wire being fixed to the cardiac implant device and thereby for guiding the support portion of the distal end of the elongated sheath along said guiding wire and to support the support portion against the cardiac implant device.

2. The medical securing device of claim 1, wherein the medical securing device comprises additionally a retrieval device having a retrieval unit, being a retriever, at a distal end thereof, said retrieval device extending from said sheath and said retrieval unit is configured to capture a portion of the securing member introduced, and to secure the portion of the securing member to the cardiac implant device and/or to the annulus of the valve.

3. The medical securing device of claim 2, wherein the medical securing device is configured to extend the retrieval unit and the securing member beyond a distal part of the cardiac implant device in said longitudinal direction, and the retrieval unit is configured to capture the portion of the securing member, whereby the portion of the securing member can be pulled towards the retrieval device to form a protrusion portion or bridge with said portion of the securing member at least partially towards, over or across said distal part of said cardiac implant device between said securing member introduction device and said retrieval device.

4. The medical securing device of claim 2, wherein said retrieval device and/or said securing member introduction device comprises a tip portion, being a penetrator, configured for penetrating and/or puncturing into or through the tissue.

5. The medical securing device of claim 2, wherein the distal end of the elongated sheath comprises a guiding trail and a tip portion of the securing member introduction device comprises a projection as a counterpart for said guiding trail, where said guiding trail and projection are thereby configured to guide said tip portion of the securing member introduction device to pierce the tissue without substantive twisting around the longitudinal axis of the tip portion of the securing member introduction device or wherein the tip portion of the retrieval device comprises a projection as a counterpart for said guiding trail, where said guiding trail and projection are thereby configured to guide said tip portion of the retrieval device.

6. The medical securing device of claim 2, wherein said retrieval device and said securing member introduction device are separated by a radial distance, substantially perpendicular to said longitudinal direction, whereby said retrieval device and said securing member introduction device are positionable on either side of said cardiac implant device in said radial direction.

7. The medical securing device of claim 2, wherein said retrieval unit comprises a loop for circumflexing said portion of the securing member.

8. The medical securing device of claim 2, wherein said retrieval unit comprises a magnet, and said securing member comprises a metal portion to be attracted by said magnet.

9. The medical securing device of claim 2, wherein said retrieval unit and/or said retrieval device is movable towards said securing member introduction device across said distal part, after having pierced the tissue.

10. The medical securing device of claim 2, wherein said securing member introduction device is movable towards said retrieval unit and/or said retrieval device across said distal part or wherein said retrieval unit and/or said retrieval device is movable towards said securing member introduction device, after having pierced tissue.

11. The medical securing device of claim 2, wherein said retrieval unit comprises a shape memory material being resiliently biased to move towards said securing member introduction device when being pushed out from said retrieval device.

12. The medical securing device of claim 2, wherein said retrieval device and/or retrieval unit are independently movable from said securing member introduction device in said longitudinal direction.

13. The medical securing device of claim 3, wherein said retrieval device and said securing member introduction device are configured to be extended from said sheath beyond the cardiac implant device.

14. The medical securing device of claim 1, wherein the elongated sheath together with the guiding wire of the cardiac implant device is configured to provides a system for applying counterforce for the introduction movement of the securing member to the cardiac implant device and thereby for securing or supporting or stabilizing the support portion of the distal end of the elongated sheath to the cardiac implant device.

15. The medical securing device of claim 1, wherein the elongated sheath comprises a conduit between the proximal and distal ends thereof for introducing under pressure into the distal end or to the support portion of the elongated sheath in order to suck and thereby to support the support portion against the cardiac implant device or to the tissue via the force induced by the under pressure and/or for applying counterforce for the introduction movement of the securing member.

16. The medical securing device of claim 1, wherein the distal end of the elongated sheath comprises a locking member, being a lock, configured to lock the distal end of the elongated sheath to the cardiac implant device or to the tissue.

17. The medical securing device of claim 1, wherein said securing member comprises a distal increased diameter portion to be captured by said retrieval unit.

18. The medical securing device of claim 1, wherein said securing member comprises a proximal increased diameter portion to be engaged by a pusher movable inside said securing member introduction device, for pushing said securing member distally from said securing member introduction device.

19. The medical securing device of claim 1, wherein the proximal end of the elongated sheath comprises an operation arm for moving the distal end of the securing member introduction device thereby introducing the securing member to the cardiac implant device thereby introducing the securing member and/or for moving the distal end of the retrieval device and thereby capturing a portion of the securing member and securing the portion of the securing member to the cardiac implant device and/or to the annulus of the valve.

20. The medical securing device of claim 1, wherein the distal end of the securing member introduction device is configured to introduce at least a portion of the securing member to the upper portion and/or lower portion of the cardiac implant device and/or into the annulus of the valve.

21. The medical securing device of claim 1, wherein the distal end of the elongated sheath comprises a recess for supporting the distal end of the elongated sheath to the upper or lower portion of the cardiac implant device during the introduction of the securing member.

22. The medical securing device of claim 1, wherein the distal end of the securing member introduction device comprises a design, which is configured to introduce the securing member in the angle in relation the upper portion of the cardiac implant device or wherein the distal end of the securing member introduction device is configured to be controlled to introduce the securing member in the angle in relation the upper portion of the cardiac implant device so that the securing member extends through the annulus of the valve and bends at least partially around or partially into the lower portion of the cardiac implant device.

23. The medical securing device of claim 1, wherein the securing member is one of the following:
    suture,
    staple the one end of which is bendable at least partially around or into the cardiac implant device under the pressing force induced by the distal end of the first stem and/or counterpart portion of the second stem,
    staple having at least one hook-shaped end to be introduced at least partially around or into the cardiac implant device,
    helical clip,
    locking cup,
    spring clip, or
    circular clip.

24. The medical securing device of claim 23, wherein the securing member comprises shape memory material, metal or polymer.

25. The medical securing device of claim 1, wherein the medical securing device is a catheter-operated or cannula-operated or open-heart operated medical securing device.

* * * * *